(12) United States Patent
deCharms

(10) Patent No.: US 9,241,665 B2
(45) Date of Patent: Jan. 26, 2016

(54) METHODS AND SYSTEMS FOR QUANTITATIVE MEASUREMENT OF MENTAL STATES

(71) Applicant: Richard Christopher deCharms, San Francisco, CA (US)

(72) Inventor: Richard Christopher deCharms, San Francisco, CA (US)

(*) Notice: Subject to any disclaimer, the term of this patent is extended or adjusted under 35 U.S.C. 154(b) by 0 days.

(21) Appl. No.: 14/599,221

(22) Filed: Jan. 16, 2015

(65) Prior Publication Data

US 2015/0133812 A1    May 14, 2015

Related U.S. Application Data

(63) Continuation of application No. PCT/US2013/070189, filed on Nov. 14, 2013.

(60) Provisional application No. 61/726,552, filed on Nov. 14, 2012.

(51) Int. Cl.
*A61B 5/00* (2006.01)
*A61B 19/00* (2006.01)
*A61B 5/16* (2006.01)

(52) U.S. Cl.
CPC .............. *A61B 5/4824* (2013.01); *A61B 5/165* (2013.01); *A61B 5/7405* (2013.01); *A61B 5/4848* (2013.01)

(58) Field of Classification Search
CPC ........................................................ A61B 5/00
USPC ........................................ 600/557, 559, 552
See application file for complete search history.

(56) References Cited

U.S. PATENT DOCUMENTS

| | | | | |
|---|---|---|---|---|
| 4,844,091 A * | 7/1989 | Bellak | | 600/557 |
| 5,191,896 A * | 3/1993 | Gafni et al. | | 600/555 |
| 5,381,805 A * | 1/1995 | Tuckett et al. | | 600/552 |
| 5,522,386 A * | 6/1996 | Lerner | | 600/547 |
| 6,113,552 A | 9/2000 | Shimazu et al. | | |
| 6,146,334 A | 11/2000 | Laserow | | |
| 6,654,632 B2 * | 11/2003 | Lange et al. | | 600/544 |
| 6,709,406 B2 | 3/2004 | Laserow | | |
| 7,399,281 B2 | 7/2008 | Shimazu et al. | | |
| 8,046,241 B1 * | 10/2011 | Dodson | | 705/2 |
| 8,512,240 B1 * | 8/2013 | Zuckerman-Stark et al. | | 600/301 |
| 2002/0068986 A1 * | 6/2002 | Mouline | | 700/94 |
| 2003/0233053 A1 * | 12/2003 | Woolf et al. | | 600/553 |
| 2006/0052720 A1 * | 3/2006 | Ross et al. | | 600/554 |
| 2010/0166660 A1 * | 7/2010 | Porreca et al. | | 424/9.2 |
| 2015/0105688 A1 * | 4/2015 | Ross | | 600/557 |

OTHER PUBLICATIONS

International Search Report for International Application No. PCT/US13/70189, Authorized Officer, Young, Lee W., Mar. 21, 2014, 4 pages.
Moon, Kihwan, Authorized officer, International Bureau of WIPO, International Preliminary Report on Patentability for International Application No. PCT/US13/070189, issued May 19, 2015, 6 pages.

* cited by examiner

*Primary Examiner* — Rene Towa
*Assistant Examiner* — May Abouelela
(74) *Attorney, Agent, or Firm* — Krenz Patent Law, LLC

(57) ABSTRACT

Methods and systems are disclosed for quantitatively assessing mental states and/or characteristics of an individual. Specific mental states and/or characteristics, or properties thereof may, in some embodiments, be associated with one or more stimuli. In some embodiments, such stimuli may be administered to an individual, whereupon the individual's responses are usable to determine one or more aspects of the individual's mental affect. Some of the disclosed methods and systems are based at least in part on computerized and computer-associated devices.

22 Claims, 10 Drawing Sheets

Sign up and answer questions about your pain to receive your personal NeuroType® PainReport.

See how your pain compares with others who have chronic pain.

Find out how many others have your pain conditions.

Gain insight into your own pain experience.

Your Report

①     CURRENT PAIN/PAIN GROUP

Your PainScale Score is    Moderate

■ Less pain than you   ■ You   ■ More pain than you

Your pain is at the 14% percentile within your group. Your pain is currently worse than 14% of people with pain, better than 86%

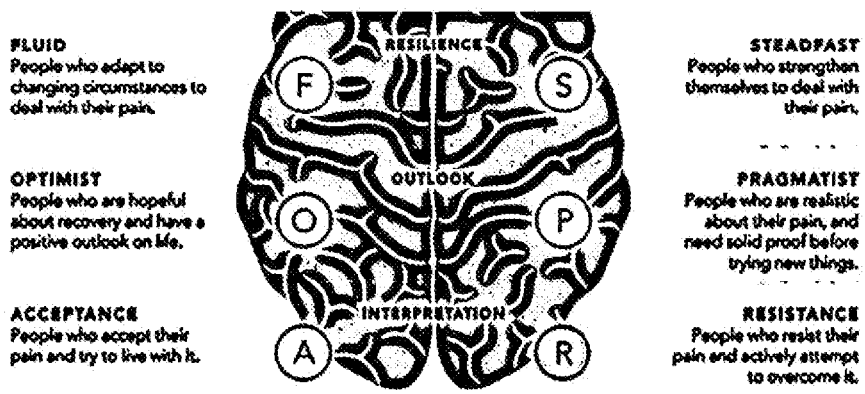

Your Neurotype Clarity

Your NeuroType indicates both your type, and also the strength of your type — that is, how clear you are in each NeuroType component over its opposite. This is known as the NeuroType Clarity, or NC. The bar graph below charts your NC results. Note that a longer bar suggests you are quite clear, while a shorter bar suggests you are less clear.

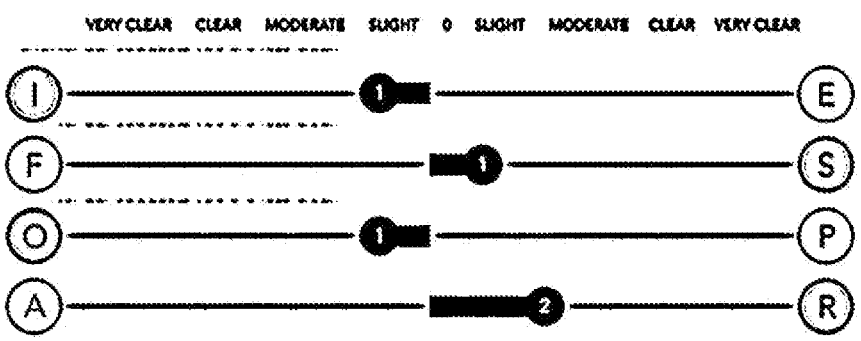

⑤ YOUR NEUROTYPE VS. PAIN POPULATION

Your Neurotype is connected to the four other Neurotypes most similar to you.

Average Within Your Pain Group is

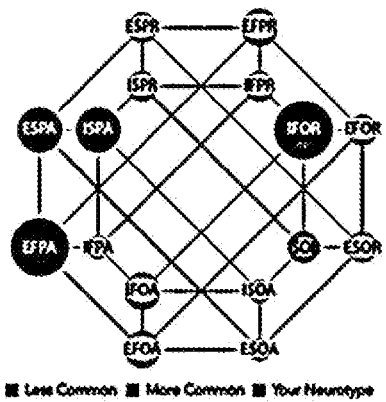

■ Less Common ■ More Common ■ Your Neurotype

People with your neurotype (ISOR) make up 5% of the pain population.

FIG. 4D

METHODS AND SYSTEMS FOR QUANTITATIVE MEASUREMENT OF MENTAL STATES

CROSS-REFERENCE

This application is a continuation of International Application No. PCT/US13/70189, filed Nov. 14, 2013, which claims the benefit of U.S. Provisional Application No. 61/726,552, filed Nov. 14, 2012, both of which applications are incorporated herein by reference.

This application is related to the following patents and patent applications: U.S. Pat. No. 6,996,261, issued Feb. 7, 2006; U.S. Pat. No. 7,567,693, issued Jul. 28, 2009; U.S. application Ser. No. 13/366,244, filed Feb. 3, 2012; U.S. application Ser. No. 13/662,398, filed Oct. 26, 2012; U.S. application Ser. No. 13/889,304, filed May 7, 2013; U.S. application Ser. No. 13/346,553, filed Jan. 9, 2012; U.S. application Ser. No. 13/815,533, filed Mar. 7, 2013; and U.S. application Ser. No. 13/878,192, filed Apr. 5, 2013, which are incorporated herein by reference.

FIELD OF THE INVENTION

The present invention relates to methods, devices, and systems for measuring mental or cognitive states of a subject, such as the intensity of pain, depression, anxiety, craving, or other mental states, particularly in the human brain and nervous system and therapeutic and diagnostic applications relating thereto.

BACKGROUND OF THE INVENTION

The quantitative and objective assessment of a person's mental state has broad applicability in several disciplines. For example, the measurement of intensity of pain in a person, their level of depression, their level of anxiety, or their level of happiness is of substantial use in a variety of contexts, including the monitoring of patients over time, measurement of symptom severity for medical treatment, the selection of treatment modalities or treatment dosages, and treatment development (e.g. pharmaceutical development).

Existing approaches for quantifying the intensity, severity or characteristics of mental states and symptoms have thus far relied principally on self-report using questionnaires. Examples include:

The Visual Analog Scale (VAS), in which a patient draws a mark on a line, the position of the mark indicating the level of their pain or other symptom severity, with one end indicating 'no pain' and the other end indicating 'worst imaginable pain';

The Numerical Rating Scale (NRS), in which a patient indicates their level of pain or other symptoms from 0 (no pain) to 10 (worst imaginable pain). The NRS and VAS can also be combined;

The McGill Pain Questionnaire (MPQ) a questionnaire that asks a patient to select words describing their pain from a number of groups (e.g. none/mild/moderate/severe, blinding, dull, burning, throbbing, etc.); and The Beck Depression Inventory (BDI), a questionnaire that asks patients to rate their sadness or level of depression on a variety of questions.

Another type of approach that has been used in the past has been to use quantified stimuli, and have subjects self-report their ratings of the intensity of an applied stimulus, for example using a visual analog scale or a numerical rating scale. In these cases, subjects are not rating the intensity of their symptom (e.g. intensity of their chronic pain), they are rating the intensity of the applied stimulus. In other words, entirely cognitive or mental states or characteristics, such as pain, depression, anxiety, motivation, happiness, positive affect, desire, and the like, are not adequately addressed by existing approaches.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4A-4E show an illustrative example format for communicating results of various techniques described in further detail herein.

DETAILED DESCRIPTION OF THE INVENTION

Figure 1:
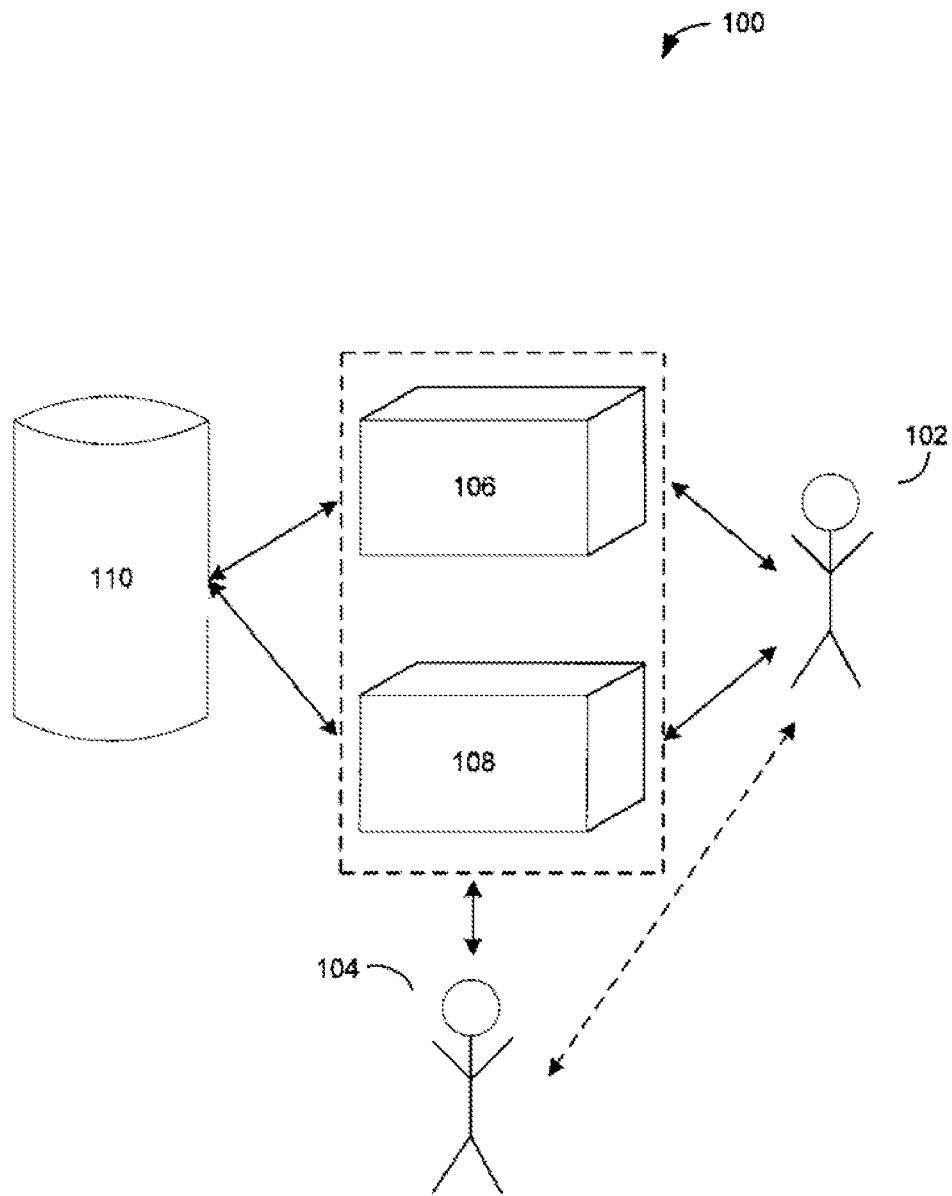
FIG. 1 shows an illustrative example of an environment in which a number of embodiments described herein may be implemented.

Techniques described, suggested and implied herein include a variety of steps, methods, and devices for quantifying (e.g., measuring) mental states and characteristics, such as medical symptoms. In particular, described herein are methods and systems for quantifying mental states and characteristics of an individual based on that individual's association of such mental states and characteristics with extrinsic stimuli or modulations thereof. In some embodiments, by way of example, one or more categories of stimuli are determined for presenting to an individual. The determined stimulus or stimuli are presented to the individual, whereupon the individual may, for example, adjust characteristics of the stimulus or stimuli (or select among the presented stimuli, in cases where multiple stimuli are presented). The individual may make such an adjustment or selection based on one or more mental characteristics or states of that individual. The selections or adjustments may be recorded and/or validated so as to generate a correlation between adjustments made (or stimulus/stimuli selected) and specific mental characteristics or states. The generated correlation may further be used to, for example, assess the individual's medical condition, develop treatment regimes for the individual, diagnose specific illnesses, and the like.

An illustrative example is provided below:

Step 1: Select a pure tone frequency audio stimulus, e.g. 1.6 kHz, to present to a person, who is a subject of investigation, experiment, or diagnosis.

Step 2: Instruct the subject that they will select the intensity level (e.g. volume) of the stimulus to match the level of their perceived pain. For example, a 'match' may be described to the person as a level at which the person would be indifferent to which is more or less pleasant, the pain or the auditory stimulus—if the patient had to live with either their pain or with the continuous auditory stimulus over a period of time, they would have no preference. If the stimulus were just a little more intense then they would prefer the pain, and if the stimulus were just a little less intense then they would prefer the stimulus.

Step 3: Allow the subject to select the stimulus to 'match' the intensity using a device providing for different intensities, for example by providing the person with a way of adjusting the volume of the auditory stimulus, or by providing the person with different intensity stimuli to choose between.

Step 4: The stimulus intensity may then optionally be used as a quantitative indication of the person's level of pain. For example, at a given moment the person may have a level of pain corresponding with a 30 dB auditory stimulus, and at a later time when their pain is more intense they may have a level of pain corresponding to a 40 dB auditory stimulus.

A variety of additional steps and methods are described herein. The described approaches are fundamentally superior to the described in the prior art in a number of ways. For example, the stimulus level selected is 'anchored' in a more meaningful way to the level of pain perceived by the stimulus, and it communicates more useful information to another (second) person (e.g., medical personnel or evaluator). As a further example, if a subject rated their pain as a '3' on a scale of 0 to 10 where 0 is no pain and 10 is the worst pain that the person can imagine, a second person upon hearing this would have little understanding of what the number '3' means to the subject. However, if the subject rated their pain as equivalent in intensity or unpleasantness to the unpleasantness of a 30 dB noise, the second person could also listen to the same 30 dB noise and gain a greater understanding of the pain being experienced by the subject. Furthermore, if a large number of people have previously compared the pain they experienced using standardized stimuli with auditory stimuli in this way, then the stimulus level chosen by a subject can be calibrated quantitatively with respect to the prior people's reports, and therefore understood more clearly.

Stimulus Selection

The stimuli to be received by a subject for matching may be selected or custom-created prior to presentation for matching. In some embodiments, the person selecting the stimulus may select the parameters or qualities of the stimulus to best represent or be similar to the internal mental state that they will be matched to. For example, some subjects find that a burning pain is more similar to a high pitch tone, whereas a pressure pain is more similar to a low pitch tone.

Auditory Selection: The person selecting the stimulus may adjust the frequency of a tone using a computer-controlled or other method to best match the quality (as opposed to intensity) of their pain, selecting a high frequency for a burning pain, and a low frequency for a pressure pain. Similarly, the person selecting the stimulus may select many features of an auditory stimulus, including, but not limited to: frequency, tone, pitch, waveform, harmonics, noise, high cutoff, low cutoff, bandpass, amplitude modulation rate, amplitude modulation rate, match of amplitude modulation rate to subject heart rate or to average heart rate, match of amplitude modulation rate to subject breathing rate or to breathing heart rate. Additional features of sounds that may be selected include sound timbre.

Many commentators have attempted to decompose timbre into component attributes. For example, J. F. Schouten (1968, 42) describes the "elusive attributes of timbre" as "determined by at least five major acoustic parameters", which Robert Erickson (1975) finds "scaled to the concerns of much contemporary music":

1. The range between tonal and noiselike character.
2. The spectral envelope.
3. The time envelope in terms of rise, duration, and decay (ADSR—attack, decay, sustain, release).
4. The changes both of spectral envelope (formant-glide) and fundamental frequency (micro-intonation).
5. The prefix, or onset of a sound, quite dissimilar to the ensuing lasting vibration.

Erickson (1975, 6) gives a table of subjective experiences and related physical phenomena based on Schouten's five attributes:

| Subjective | Objective |
|---|---|
| Tonal character, usually pitched | Periodic sound |
| Noisy, with or without some tonal character, including rustle noise | Noise, including random pulses characterized by the rustle time (the mean interval between pulses) |
| Coloration | Spectral envelope |
| Beginning/ending | Physical rise and decay time |
| Coloration glide or formant glide | Change of spectral envelope |
| Microintonation | Small change (one up and down) in frequency |
| Vibrato | Frequency modulation |
| Tremolo | Amplitude modulation |
| Attack | Prefix |
| Final sound | Suffix |

Harmonics:

The richness of a sound or note produced by a musical instrument is sometimes described in terms of a sum of a number of distinct frequencies. The lowest frequency is called the fundamental frequency and the pitch it produces is used to name the note, but the fundamental frequency is not always the dominant frequency. The dominant frequency is the frequency that is most heard, and it is always a multiple of the fundamental frequency. For example, the dominant frequency for the transverse flute is double the fundamental frequency. Other significant frequencies are called overtones of the fundamental frequency, which may include harmonics and partials. Harmonics are whole number multiples of the fundamental frequency, such as ×2, ×3, ×4, etc. Partials are other overtones. Sometimes there are also subharmonics at whole number divisions of the fundamental frequency. Most western instruments produce harmonic sounds, but many instruments produce partials and inharmonic tones, such as cymbals and other indefinite-pitched instruments.

When the orchestral tuning note is played, the sound is a combination of 440 Hz, 880 Hz, 1320 Hz, 1760 Hz and so on. Each instrument in the orchestra will produce a different combination of these frequencies, as well as harmonics and overtones. The sound waves of the different frequencies will overlap and combine, and it is the balance of these amplitudes that is a major factor in the characteristic sound of each instrument.

Selection of Stimuli Based on Valence:

Stimuli may be selected based upon their valence. For example, to represent an unpleasant mental experience such as pain a stimulus may be selected that is judged as aversive.

For example, subjects may find audio stimuli that have a square wave or saw tooth wave to be more aversive than pure tone stimuli. Other types of stimuli may also be selected based upon the estimation of the person selecting the stimulus as to their valence: positive, negative, or reflective of some other feature of the mental experience to be measured. The person selecting the stimulus may decide the valence of the stimulus based upon the reactions of the stimulus when it was presented to prior subjects, for example when subjects were asked to rate its valence or rate its valence in comparison with other stimuli.

Positive stimuli may also be used in the 'negative'. For example, a subject may be asked how much money (a positive stimulus) they would require in order to endure their pain or other negative mental state for a period of time. In this way, indifference is measured between the presence of one stimulus (e.g. the pain) and the lack or loss of another stimulus (e.g. money, food, drink, pleasant image, sight, other positive stimulus or experience).

Types of Stimuli

While many of the examples provided herein employ auditory stimuli, many other types of stimuli may be used and are contemplated herein. For example, the stimuli may be auditory, tactile (touch), vibratory, pressure, temperature (warm, cold, neutral), taste, smell, body position, movement speed, visual stimuli including images and video, or any combination thereof. In particular, any stimulus that is perceived as aversive, unpleasant, or negative can be used as a basis for comparison. Specific examples of information include instructions to perform a task or how to perform a task, movies, or stereoscopic virtual reality stimuli viewed through stereo viewers and designed to simulate certain circumstances or experiences. Further examples include games played by the subject, such as computer games. Some of such types of stimuli for selection are described in further detail below.

Speech Stimulus:

A speech stimulus may be selected to include certain words, sentences, content or affect, presented using sound or visually. For example, happy or sad stories may be used, or descriptions of specific events.

Tactile Stimulus:

A tactile stimulus may be selected to include pressure level for a constant stimulus, frequency for a vibratory stimulus, temperature. For vibratory stimuli all of the components already described for auditory stimuli may additionally be selected.

Smell Selection:

Single or multi-component odors may be selected using natural or artificial odorants, aromatherapy, aromatics.

Taste Selection:

Tastes may be selected using all of the culinary arts, as well as using concentrations of specific ingredients such as salt concentration or sugar concentration.

Visual Stimulus Selection:

Visual stimuli may be selected based on color, pattern, image content, video content, motion content, direction, orientation, size or other features. Visual stimuli may also include images such as images of people's faces that may be indicative of emotions.

Stimuli Representing Features of Mental Experience

In some embodiments, stimuli may be specifically designed and/or selected to mimic or represent one or many features of a mental experience.

Multi-Feature Stimuli:

Stimuli may be selected to represent a plurality of features of a mental experience. For example, if the mental experience of pain contains different qualities (burning pain, stabbing pain, pressure pain) then different stimuli may be selected and adjusted to reflect the characteristics and intensity of these different qualities. These stimuli may then be combined to create a representation of the entire mental experience. For example, if a subject experiences burning pain represented by a high tone and pressure pain represented by a low tone, then their total pain may be represented by the combination of these two sounds. Similarly, if a subject experiences pain from a plurality of different body parts, then their total pain may be represented by a multichannel sound (e.g. stereo, etc.) with multiple components, or a single channel sound with the component auditory waveforms added or combined.

Example Stimulus Representations:

The table below presents some examples of stimuli that may be particularly effective in representing particular mental experiences. Any of the unpleasant stimuli may be matched with unpleasant mental experiences, and pleasant stimuli may be matched with pleasant mental experiences. This invention also discloses the process of allowing subjects to choose stimuli that they perceive to be similar to the mental experience that they wish to match, and the process of using these stimuli for matching according to the current invention either in the same subject or in a different subject.

| Mental Experience | Stimuli |
| --- | --- |
| Pain | Sounds |
| Sharp pain | Unpleasant high frequency sounds |
| Pressure pain | Unpleasant low frequency sounds |
| Throbbing pain | Amplitude modulated sounds, e.g. modulated at heart rate and/or breathing rate. |
| Pain | Painful pressure |
| Pain | Painful heat or Painful cold |
| Pain | Cold plus blood constriction (cold pressor) |
| Pain | Laser stimulus |
| Pain | Imagined stimuli including any of the above, or other painful stimuli/situations |
| Depression | Very low frequency sounds |
| Anxiety | Unpleasant noise, including white noise, pink noise, bandpass filtered noise. |
| Craving | Smells, sounds, images, video related to the craved object. For example, images, video or sounds of cigarettes or smoking. |
| Tinnitus | Pure tone or band-filtered noise designed to mimic tinnitus sensation. |
| Phobias | Images, virtual reality stimuli or video of the feared object, for example images or representations of faces for social phobia, snakes, planes, heights. |
| OCD/compulsions | Images, sounds, video representing the compulsive thought, for example images of an unclean item, bloody item, door open, stove on. |
| Psychosis | Voices or sounds representing auditory hallucinations experienced by the subject. |

Identity of the Entity or Entities Selecting the Stimulus

In some embodiments, the entity selecting the stimulus to be received by a subject may be selected prior to presentation for matching by the subject who will receive the stimulus. In other words, the stimulus may be selected by the subject himor herself. In some embodiments, the person selecting the stimulus for matching by the subject may be a person other than the subject (e.g., an evaluator of the subject's mental experience). For example, the evaluator may be a healthcare or other professional. In some embodiments, the evaluator may be a computer or computer-connected device that may, in some of such embodiments, automatically evaluate the mental experience of the subject and/or automatically select the most appropriate stimulus or stimuli from which the subject will choose, based, e.g., an initial analysis (in some cases by the computer or computer-connected device) on the subject's extant mental state and/or characteristics.

In some embodiments, the stimuli to be received by a subject may be selected prior to presentation for matching based on data (e.g., collective, crowd-sourced and/or externally validated data) from other subjects or evaluators. For example, if many subjects have selected the parameters of an auditory or other stimulus that they feel best represents a particular type of pain, for example a high pitch pure tone for burning pain, then this stimulus may be used in other future patients. The stimuli may also be used based upon calibration experiments in subjects designed to best approximate certain mental experiences with certain stimuli based upon average responses. Such data may, in some embodiments, be stored within a computerized data store (e.g., a database), and accessible using programmatic or other methods (e.g., through a user interface, Web-based application, or smartphone/tablet application) for retrieving such data.

Methods for Selecting a Stimulus

Stimuli may be selected using a variety of methods and devices, including computer-facilitated or computer-implemented methods and devices. For example, stimuli may be selected using real or virtual dials, sliders or switches designed to select among the parameters and qualities described in the section on stimulus selection. Additionally, stimulus buttons or icons may be used to select pre-created stimuli or types of stimuli. The facility for stimulus selection and/or manipulation may be presented physically, virtually, or in some combination thereof. In some embodiments, such facilities may be enabled (e.g., presented) via a computer or other device display (which in some embodiments may be interactive, e.g. via resistive or capacitive touch), physical dials, sliders, buttons, and the like.

Device/Subject Calibration and Stimulus Shaping

The stimuli to be presented to a given subject using a given device may be calibrated so that what is perceived by the subject is similar to a desired characteristic. For example, if the stimulus is a broadband noise, then the frequency response curve of the device presenting the stimulus, and the audiogram of the subject receiving the stimulus both contribute to what is perceived by the subject. The frequency response curve and/or distortion of the presentation device may be calibrated or measured so that the stimulus presented can be made to more accurately match the desired stimulus, taking into account the device. For example, if the output device produces broadband noise or a variety of narrow band stimuli such as pure tones at different frequencies, and the same device or a different device records the output of the output device, then the output device can be calibrated, creating a frequency response curve, and other calibration measures. This is described in Audio in Media, Stanley Elton, included here by reference, to include methods for audio recording, production, calibration, and general stimulus creation methods.

Once a device has been calibrated to create a desired stimulus, then replicas of that device may be used in additional subjects. For example, if a particular stimulus has been tested using a given mobile device and headphone combination, then this combination can be provided to future subjects in order to achieve or produce a similar or calibrated stimulus.

The input of the subject may also be calibrated, for example by creating an audiogram in the subject using the stimulation device, or a sound level threshold. Once this has been completed, then a stimulus may be presented to the subject at a level of intensity in subjective terms for the subject. A stimulus intensity (e.g. dBSPL) may thereby presented at a given sensation level (e.g. dBSL). Also, a stimulus may be shaped using an optimal or other filter to correct for the subject's audiogram, or its deviation from a normal audiogram.

Similar processes may be used to calibrate other types of stimuli. For example, painful pressure or painful heat stimuli may be calibrated to produce an average level of perceived pain intensity in a group of people e.g. 0 out of 10, 1 out of ten etc. up to 10 out of 10. In this way, the intensity of a stimulus may be pre-calibrated based upon the response of a large number of subjects. Similarly, audio stimuli may be created that produce an average level of perceived unpleasantness in a group of subjects of a desired value. By selecting multiple stimuli of varying intensity or other parameters, it is possible to create a psychophysical curve. Then, stimuli may be selected based upon their position on this curve (eg audio stimulus volume) to produce a desired, calibrated level of pain or unpleasantness in a target group of subjects such as healthy subjects, adults, children, men, women, people with a particular symptom or disease condition such as pain, depression, anxiety, etc.

Once calibration has been completed for a piece of hardware or device using an initial group of people, that device may be sold or provided to later subjects in order to achieve greater accuracy in assessing those later subjects. A calibrated device that may be provided in combination with this invention is a calibrated microphone. A calibrated device that may be provided in combination with this invention is a calibrated speaker. A calibrated device that may be provided in combination with this invention is a calibrated headphone. A calibrated device that may be provided in combination with this invention is a calibrated earbud. A calibrated device that may be provided in combination with this invention is a calibrated sound-cancelling headphone. A calibrated device that may be provided in combination with this invention is a calibrated mobile phone. A calibrated device that may be provided in combination with this invention is a calibrated PDA. A calibrated device that may be provided in combination with this invention is a calibrated tablet. A calibrated device that may be provided in combination with this invention is a calibrated computer. A calibrated device that may be provided in combination with this invention is a calibrated wearable computing device.

Once calibration has been completed for a particular stimulus or type of stimulus, that stimulus or type of stimulus may be sold or provided to other subjects in order to achieve greater accuracy. A calibrated stimulus that may be provided in combination with this invention is a particular sound. A calibrated stimulus that may be provided in combination with this invention is particular painful stimulus such as painful heat or painful pressure. Some examples of calibrated stimuli that may be used in this fashion include, but are not limited to:

Sounds with a frequency of 100, 200, 400, 800, 1600, 3200, 6400 Hz or any increment of these frequencies following a standard 12-tone or octave scale. Other frequencies include any of those corresponding to a standard keyboard, following the equation:

$$f(n) = \left(\sqrt[12]{2}\right)^{n-49} \times 440 \text{ Hz}$$

which provides the frequency f of the nth key; and

Sounds that include pure tones, harmonics of pure tones, square wave waveforms, triangle wave waveforms, saw-tooth waveforms, bandpass noise white noise, pink noise, FM sweeps, AM sweeps, human-created or artificially created words, phonemes or vowel sounds.

Methods/Devices for Presenting, Communicating and Storing a Stimulus

Examples of ways of communicating stimuli include, but are not limited to displaying information to the subject, playing audio for the subject, providing an agent for the subject to smell, applying a physical force to the subject (e.g., a pressure or vibration or proprioceptive stimulus), administering a drug to the subject, and causing a physical sensation for the subject (e.g., cold, hot, pain, electrical charge, etc.).

A variety of types of devices may be used, individually or in combination, for presenting stimuli. For example, stimuli may be presented using a computer, telephone, cell phone, smart phone, headphones, ear buds, sound cancelling headphones, calibrated headphones, tablet computer, PDA, Internet browser, Web application, mobile application, computerized user interface, social network, watch, virtual or augmented reality goggles or other devices, thermal probe, pneumatic pressure probe, mechanical pressure probe. The stimuli (or data representing such stimuli) may be stored either directly on the delivery/presentation device(s) itself (e.g., in non-transitory computer-readable media incident to, colocated or otherwise incident to the delivery/presentation device). In some embodiments, stimuli or representations thereof are stored or represented remotely from the delivery/presentation device(s), e.g., in a data store of a computing resource provider. In such embodiments, devices may connect to (and retrieve the stimuli and associated data from) the entity storing the stimuli and associated data via any appropriate direct or programmatic interface. Examples include APIs, WiFi, Bluetooth, cellular protocols (such as LTE, HSPA, GSM, CDMA, WiMax and the like), Web services (including those using representation state transfer (REST) and/or Simple Object Access Protocol (SOAP)), Web interfaces (programmatic and otherwise), network protocols such as TCP/IP, and the like. Stimuli may be stored in any appropriate format, including audio file formats such as MP3, MP4, AAC, video file formats such as MPEG, and others.

Selecting Timing and Location for Presenting a Stimulus

Time-Related Averaging:

The time of presentation of a stimulus may be pre-selected. For example, the stimulus timing may be selected to include:

1) Presenting the stimulus at a pre-defined time of day, optionally repeatedly
2) Presenting the stimulus at a selected time interval into the future
3) Presenting the stimulus at a selected time interval after another stimulus
4) Presenting the stimulus at a selected inter-stimulus interval This approach may be repeated multiple times in the same subject, or may be repeated in multiple subjects, to make multiple measurements of the matching stimulus at each time point, or in each time range before and/or after an event. These measurements may then be used to form an average of the matching stimulus parameters for each type of time point. For example, the measure may be averaged for 9 AM each day, or for Mondays, or for a given time after another stimulus or event has occurred, or for a given time after a subject has undertaken an activity.

Event-Related Averaging:

The time of presentation of a stimulus may be pre-selected in relation to the time of a specified event. For example, the stimulus timing may be selected to include:

1) Presenting the stimulus at a pre-defined interval before and/or after an event. For example, presenting the stimulus to allow the subject to perform matching and thereby rate their mental experience or symptoms every ten minutes up to a maximum of 240 minutes after the subject receives a drug or treatment that is intended to affect their symptoms.
2) Presenting the stimulus at random times before and/or after an event that are designed to sample the pre or post-event time.

This approach may be repeated multiple times in the same subject, or may be repeated in multiple subjects, to make multiple measurements of the matching stimulus at each time point, or in each time range before and/or after an event. These measurements may then be used to form an average of the matching stimulus parameters for each time point before and/or after the event. For example, the measure may be averaged for 30 minutes after the event of taking a pain-relieving medication, or for a given time after the event of a subject has undertaken an activity that might increase their pain such as exercise, a painful stimulus, or a medical procedure, or might decrease their pain such as some form of treatment.

Location-Related Averaging:

The location of presentation of a stimulus may be pre-selected. For example, the stimulus location may be selected to include:

1) presenting the stimulus when the subject is in a particular location or defined perimeter
2) not presenting the stimulus when the subject is in a particular location or defined perimeter This approach may be repeated multiple times in the same subject, or may be repeated in multiple subjects, to make multiple measurements of the matching stimulus at each location, or in each location range. These measurements may then be used to form an average of the matching stimulus parameters for each location. For example, the measure may be averaged for measurements at home, at work, or at a location identified using a computer (e.g. a computer configured to know a subjects location relative to signal such as GPS signal, a cellular signal, or a wife signal).

Each of the approaches described for averaging may be performed on selected groups of subjects, and the results may be compared for different groups. For example, a curve may be formed representing the average pain decrease in a group of subjects vs. time before and after presentation of one medication designed to decrease pain vs. a different medication designed to decrease pain. Averaging may also be selected based upon the characteristics of the subject, for example symptom severity, diagnosis, male/female, age, based upon a personality assessment test or psychological test, based upon performance testing, or based on other parameters. Thereby, it may be possible to compare the responses to a given event, intervention, drug or treatment over time in different groups of patients. This may be used as a method of inferring the likely outcome of a medication in new subject or group of subjects.

Instructing Subjects/People

Subjects may be instructed as to how to perform matching between their internal, mental experience and a stimulus. For example, a subject may instructed to this of a match as the level of the stimulus where they are indifferent to the intensity or unpleasantness level of the stimulus vs. their own mental experience. For example, people communicate the value of a good through currency, an external unit of measure that can be used to communicate value between people. A person chooses a unit of value for an object, e.g. $4000 for a piano or for a computer, to indicate that they would value the object equally with that amount of currency. Similarly, a person can match the level of a stimulus to a mental experience so that they have matching valence or value. A person can choose the level of an unpleasant stimulus, such as an unpleasant sound, to match their internal mental experience, such as their level of chronic pain, so that they would value to two as being equally unpleasant, or so that they would be indifferent to choosing one or the other. Subjects may be provided with instructions such as these to learn to create matches. Subjects may be trained to create accurate and reproducible matches by learning to match other types of stimuli, for example matching the level of two different sounds so that they are equally unpleasant, or matching the level of a sound with a painful stimulus so that they are equally unpleasant. By doing this repeatedly and receiving feedback on their reproducibility, subjects can come to learn to produce accurate matches.

Presenting a Stimulus

Stimuli may be presented to subjects. This step may include any of the stimuli disclosed herein. This step may include future types of stimuli later developed to match other mental experiences. Stimuli may be presented with the devices disclosed herein or devices known in the art.

Control Over Stimulus Parameters:

The parameters of the stimuli, including their intensity, may be controlled. Examples of control include controlling the amplitude, intensity, or volume of a stimulus. For example, the volume of an auditory stimulus may be controlled. Other parameters of a stimulus may also be controlled. The control over the stimulus parameters may take place prior to the presentation of the stimulus. The control over the stimulus parameters may take place during the presentation of the stimulus, for example adjusting volume while listening to the stimulus. The control over the stimulus parameters may take place after the presentation of the stimulus, for example adjusting the volume down if it was too loud, or up if it was too quiet. The adjustment of the stimulus parameters may be completed by the subject or by an evaluator. In some embodiments the stimulus is limited to ranges detectable by a human subject. In some embodiments the stimulus is limited based on pre-defined safety concerns (e.g. a sound stimulus can be limited to below a threshold that would cause hearing damage).

Repetition:

Stimuli may be presented multiple times to subjects, or multiple stimuli may be presented to subjects, to achieve multiple measurements.

Matching

The subject may match the stimulus to their internal mental experience. For example, if the subject has chronic pain, they may adjust the volume of the stimulus until it matches the level of pain that they experience, following instructions that they have been provided. Similarly, many other types of mental experience may be matched with other types of stimuli, as provided herein. In each case, a 'match' may be obtained when the stimulus is deemed by the subject to be equivalent to the mental experience. Alternatively, matching may take place using any of a variety of psychophysical methods, such as two alternative forced choice (subject decides which of two stimuli is more like their mental experience), method of constant stimuli, method of limits, method of adjustment, adaptive psychophysical methods, staircase procedures, magnitude estimation. These have been described in texts including:

Psychophysics: A Practical Introduction by Frederick A. A. Kingdom and Nicolaas Prins Signal Detection Theory and Psychophysics by David Marvin Green and John A. Swets Both texts are included here by reference.

Subjects may also use procedures to estimate their mental experience that do not involve explicit matching, for example selecting stimuli that are above their level of mental experience, or selecting stimuli that are different from it in other respects.

Averaging/Estimation of Match

When stimuli are presented multiple times, the average response of the subject may be computed. For instance, if a subject selects a tone at 32 dB, 34 dB and 36 dB as a match to his level of experienced pain on multiple trials, the mean of 34 dB may be selected as the best match, and the variance, standard deviation and other statistical measures may be computed. In addition, different average measures may be compared to determine whether they are statistically significantly different, for example using t-tests, anova, regression, and other statistical methods.

Validation and Measurement

In order to validate this method, a plurality of subjects may be tested using a stimulus, or a group of stimuli, to assay their mental experiences and produce group estimates of the groups' mental experiences. For example, a group of patients with a defined condition, such as back pain, fibromyalgia, or some other pain condition may be tested using a stimulus, such as a 1.6 kHz pure tone, to determine the level that they find matches their level of pain. Then the distribution of matching levels of the group may be assessed, or may be modeled mathematically, for example using a Gaussian or other distribution. This allows the comparison of a given subjects matching to a group. For example, it might be determined that a subject matches their pain with a stimulus more intense than 36% of prior subjects. See below regarding comparison.

Validation Using an Internally Generated Mental Experience:

A group of subjects may use the method provided herein to rate an internally generated mental state, such as chronic pain, depression, sadness, anxiety, fear, happiness, joy, motivation, calm, anger, craving.

For example, a group of subjects may be asked to select the 1.6 kHz square wave tone intensity in dB that best matches the unpleasantness of their chronic pain. The subjects may repeat the match ten times. If the subjects also rate external stimuli with other rating methods, such as VAS/NRS or others, then the multiple methods can be compared (e.g. comparing which has the greater reproducibility within subjects or between subjects), and mathematical relationships or correspondences can be formed between different measures (e.g. a 4 NRS rating corresponds to a 32 dB sound on average).

The reproducibility, variance, standard deviation and other statistics of the group measures may also be measured.

Once a given stimulus or type of stimulus has been precisely validated in this way, it may be used in future subjects to provide additional information. For example, once a sound stimulus such as a 1.6 Khz square wave has been validated as described in a range of subjects, the level selected by a given subject can be correlated with similar subjects in a prior group of subjects, or with a model of prior subject data, to infer the level of the subject's mental experience, for example in units of temperature or percentile, or VAS/NRS pain rating rather than in units of sound dB or stimulus parameters or intensity.

Validation Using an Externally Generated Stimulus to Produce a Mental Experience:

A group of subjects may use the method provided herein to rate an externally generated mental state, such as using a plurality of sensory stimuli. These sensory stimuli may provide a range of intensities or qualities. In this way, it may be possible to estimate the average match stimulus parameters, variability of the match stimulus parameters, and distribution of the match stimulus parameters of a range of sensory stimuli. This may make it possible to graph or mathematically model the matching stimulus parameters for different sensory stimuli. This may allow for estimates of the discriminability of different sensory stimuli, for example measurement of Cohen's D, or d-prime, and the inference of discriminability of different internally generated mental states.

For example, a group of subjects may be asked to select the 1.6 kHz square wave tone intensity in dB that best matches the unpleasantness of a 4×4 cm heat sensory stimulus applied at temperatures from 38 degrees C. to 52 degrees C., in increments of one half degree. The subjects may repeat the match for each sensory stimulus ten times. Then, it will be possible to construct a curve representing the relationship between the sensory stimulus intensity (temperature) and the sound (dB), showing the mean, variance, and linear, logarithmic or non-linear regression in either a single subject, or a group of subjects. If the subjects also rate these stimuli with other rating methods, such as VAS/NRS or others, then the multiple methods can be compared (e.g. comparing which has the greater reproducibility within subjects or between subjects), and mathematical relationships or correspondences can be formed between different measures (e.g. a 4 NRS rating corresponds to a 32 dB sound on average).

Similar procedures may be used with other types of sensory stimuli, see the section regarding types of stimuli.

The reproducibility, variance, standard deviation and other statistics of the group measures may also be measured.

Once a given stimulus or type of stimulus has been precisely validated in this way, it may be used in future subjects to provide additional information. For example, once a sound stimulus such as a 1.6 Khz square wave has been validated as described with a range of pain stimuli in a range of subjects, the level selected by a given subject can be correlated with similar subjects in a prior group of subjects, or with a model of prior subject data, to infer the level of the subject's mental experience, for example in units of temperature or VAS/NRS pain rating rather than in units of sound dB or stimulus parameters or intensity.

Validation Using Physiological Measurement:

The current invention discloses that the ratings given by single subjects or groups of subjects may be compared with and validated by physiological measures. For example, the match parameters (e.g. stimulus intensity) that a subject selects to match their mental experience caused by a range of pain stimuli may be correlated with the level of brain activation produced in a plurality of brain regions associated with pain experience. In this way, a correlation may be formed between the level, physical extent, or duration of activation produced by different mental experiences and the level of match parameters (e.g. stimulus intensity) selected by the subject for the same or a similar range of pain stimuli. This process may also be used with other types of mental experience as disclosed herein, and with internally generated mental experiences such as chronic pain, depression, anxiety, and others.

Some example physiological measurements that may be used to correlated with stimulus match parameters (e.g. stimulus intensity) include: functional magnetic resonance imaging (fMRI), cerebral blood flow including measurement using PET, ASL, other PET measures, other MRI measures, diffusion, electroencephalogram (EEG), evoked potentials, galvanic skin response (GSR), heart rate and variability, breathing rate and variability, NIRS and fNIRS, HEG, MEG, neural recording, fMRI BOLD signals, fMRI EPI signals, PET or SPECT signals, or event-related signals conditioned on sensory events/motor behaviors, or other physiological measurements. These measurements may be made using a variety of physiological recording apparatus. Examples of measurement apparati that may be used alone or in combination include, but are not limited to functional magnetic resonance imaging (fMRI), PET, SPECT, EEG (electroencephalogram) recordings or event-related electrical potentials, MEG recordings (magnetoencephalogram), electrode-based electrophysiological recording methods including single-unit, multi-unit, field potential or evoked potential recording, infrared or ultrasound based imaging methods, or other manner of measuring physiological states and processes.

Validation by Physician or Provider/Physician Report:

The measures described herein may be used in combination with a physician-generated report. The measures described herein may be used in combination with a report generated by another provider, such as a physical therapist, counselor, psychotherapist, chiropractor, acupuncturist, alternative therapy provider, psychologist, or others. The provider may provide a summary or an interpretation of the results from a patient, for example making a clinical determination of the patient's pain based on the data, or diagnosis of the patient based on the data, or a treatment plan or prescription based on the data. This data may also be combined with other clinical data, lab tests, personality test data. Similar to a radiological report, or other medical report read by a specialist, this report may lead to patient treatment recommendations, and may be billed and paid for separately and paid in total or in part to the physician or provider creating the report, possibly using pre-determined reimbursement rates from payors such as health insurers or patients or providers.

Validation Database:

The validation data accumulated through the validation process may be stored in a validation database. The validation database can interact with a device which applies the stimuli or with a computer or device that analyzes the subjects interaction with the device.

Comparison of Subject's Results to Validation Database or Model:

The results of a given subject's match data may be compared with the results in a validation database or with a mathematical model designed to mimic the data, such as a linear or non-linear regression model. The members of the database may be pre-selected based upon a plurality of criteria. For example, people in the database may be suggested who have the same disease state as the patient, or a different disease state. People may be selected who have the same or a different gender. People may be selected who have a similar or different disease, condition, level of symptom severity, age, psychological test result, or other features.

This may provide inferences. For instance, it may be possible to infer that a given woman with fibromyalgia who rates her pain at the level of a 32 dB 1.6 kHz square wave sound is at the 46th percentile of women with fibromyalgia over 50 years old.

Combination of Multiple Measures:

Multiple measures may be combined to produce a full assessment of a subject. For instance, if a person has multiple symptoms, or multiple components of a single symptom, it may be possible to assess each of their multiple symptoms or components to create a comprehensive report. For instance, if a person has pain in three body parts, it may be possible to produce a report of the intensity of pain, and how it relates to the intensity of pain in similar patients, in each of the three body parts.

Measurement of Changes Over Time and with Treatment:

It may be possible to make multiple measurements from a subject or a group of subjects over a period of time in order to assess whether their mental experience is increasing, decreasing, or staying the same. See also section on Selecting Timing. For example, in pharmaceutical or medical device testing it may be desirable to determine how much subjects' symptom levels are decreasing following treatment, and to measure a timecourse of changes, and to measure statistical significance of changes vs. baseline, or vs. a control group of subjects not receiving the same intervention.

In some embodiments the ability of a pharmaceutical to decrease a mental state (e.g. pain) can be determined across a population and integrated into a database for analyzing an individuals symptoms. For example a certain dosage of a drug might be expected to reduce pain by 50% based on a set of test data. A patient can be given the dose of the drug and measurements can be made before and after the drug administration. If a patient is not responding in a predictable way to the drug a clinition may learn about the patient's mental experience or may learn about a patients likely reporting inaccuracies.

Communication of Results

The results of the testing described in this invention may be provided to a variety of relevant parties, including the patient or subject, the physician or provider (included physical therapists, psychologists, chiropractors, alternative health providers, other health providers). In some instances it may be preferable to avoid communication of this information, for instance to insure patient privacy. Patients or providers may control their results and have power to determine whether providers or insurers receive them.

The results may be communicated in many forms. One form in which the subject's mental experience may be communicated is through providing a matching stimulus selected by a subject. For example, if a subject selects a 1.6 kHz square wave sound at 32 dB as the best match to their pain, this same stimulus may be provided to a caregiver, provider or others to communicate directly the patient's mental experience, in this case their pain level. Another form in which the subject's mental experience may be communicated is to provide one or more stimulus parameter of the matching stimulus selected by the subject. For example, the indication of 32 dB in the example just cited. Another form in which the subject's mental experience may be communicated is to provide a percentile into which the subject falls among a group of subjects. For example, the subject's selection of a 32 dB stimulus is in the 46th percentile among a group of subjects. Another form in which the subject's mental experience may be communicated is to provide a correlated level of a different sensory stimulus previously tested in a group of subjects. For example, the subject's selection of a 32 dB stimulus is correlated with any average of a 49 degree painful heat stimulus selected by previous subjects to match a 32 bB stimulus, or a given pressure pain stimulus. Another form in which the subject's mental experience may be communicated is to provide a correlated rating using a different rating instrument previously tested in a group of subjects. For example, the subject's selection of a 32 dB stimulus is correlated with any average of a 4 on a visual analog scale of pain ratings, or a 4 on a numerical rating scale of pain ratings, or a 15 on a McGill Pain Questionnaire, or a 16 on a Beck Depression Inventory (BDI), HAM-A, HAM-D. Other measures that might be used are the many symptom dianostics that currently exist or may be developed, including but not exclusive to: VAS, Visual Analogue/Numerical Ratings of Pain; MPQ, McGill Pain Questionnaire; CSQ, Coping Strategies Questionnaire; PCQ, Pain Control Questionnaire; PCS, Pain Catastrophizing Scale; MH, Mental Health; PF, Physical Functioning; Medical Outcome Study Short Form-36 Health Survey; SCL-90R, Symptom Check List-Revised; MOS-Sleep, Medical Outcome Study Measure of Sleep; SF-36, HCU, Health Care Utilization; HCUQ, HCU Questionnaire; AE, Adverse Events; AEQ, AE Questionnaire.

Combination with Treatments

This approach may be used in combination with a variety of types of treatment in order to measure treatment effectiveness. Treatments include, but are not limited to: drugs, surgery, medical devices, physical therapy, acupuncture, counseling or therapy, CBT, online treatment, support groups, therapeutic gaming, educational materials, and others.

Recommendation of Treatment, Parameters or Dosage:

This invention may be used to assess a patient's level of symptom severity, and thereby to select a type or dosage of treatment defined to be appropriate to that level of severity. This may be possible by determining the type or dosage of treatment predicted to produce a desired level of improvement or desired maximum level of residual symptoms after the treatment, based upon measurement in prior subjects. For example, a subject may be prescribed a dosage of a pharmaceutical, such as a narcotic, using a defined range of pain intensity levels that correspond to each dosage of pharmaceutical, or using a hear or non-linear relationship between pain intensity level and pharmaceutical dosage. A similar approach may be used in prescribing dosages of other types of medication for other conditions, for example for depression, anxiety, ocd, panic disorder and others. A similar approach may be used in prescribing dosages, numbers, durations, or intensities of other types of treatment for example numbers of sessions of physical therapy or counseling, stimulation parameters for TENS or spinal cord stimulation, stimulation parameters for TMS.

Examples of Applicable Conditions

This invention may be used to measure the mental experience for a variety of conditions, sorted alphabetically, including but not limited to:

A

Acute stress disorder
Adjustment disorder
Adolescent antisocial behavior
Adult antisocial behavior
Adverse effects of medication-not otherwise specified
Age-related cognitive decline
Agoraphobia
Alcohol abuse
Alcohol dependence
Alcohol withdrawal
Alcoholic hallucinosis
Alzheimer's disease
Amnestic disorder
Amphetamine dependence
Amphetamine withdrawal psychosis
Anorexia nervosa
Anterograde amnesia
Antisocial personality disorder
Anxiety disorder
Anxiolytic-related disorders
Asperger syndrome
Attention deficit disorder
Attention deficit hyperactivity disorder -continued Autism
Autophagia
Avoidant personality
disorder
B Barbiturate dependence
Benzodiazepine dependence
Benzodiazepine misuse
Benzodiazepine withdrawal
Bereavement
Bibliomania
Binge eating disorder
Bipolar disorder
Bipolar I disorder
Bipolar II disorder
Body dysmorphic disorder
Borderline intellectual
functioning
Borderline personality
disorder
Brief psychotic disorder
Bulimia nervosa
C Caffeine-related disorder
Caffeine-induced sleep
disorder
*Cannabis* dependence
*Cannabis* withdrawal
Catatonic disorder
Catatonic schizophrenia
Childhood amnesia
Childhood antisocial
behavior
Circadian rhythm sleep
disorder
Cocaine dependence
Cocaine intoxication
Cognitive disorder
Communication disorder
Conduct disorder
Cotard delusion
Cyclothymia
D Delirium tremens
Depersonalization disorder
Derealization disorder
Desynchronosis
Dissociative identity disorder
(multiple personality
disorder)
Dysthymia
E EDNOS
Encopresis
Ekbom's Syndrome
(Delusional Parasitosis)
Enuresis (not due to a
general medical condition)
Erotomania
Exhibitionism
F Factitious disorder
Fregoli delusion
Fugue State
G Ganser syndrome (due to a
mental disorder)
Gender identity disorder
Generalized anxiety disorder
General adaptation syndrome
Grandiose delusions -continued

H

Hallucinogen-related
disorder
Hallucinogen persisting
perception disorder
Histrionic personality
disorder
Huntington's disease
Hypomanic episode
Hypochondriasis
I Impulse control disorder
Impulse-control disorder not
elsewhere classified
Inhalant abuse
Insomnia due to a general
medical condition
Intermittent explosive
disorder
K Kleptomania
Korsakoff's syndrome
L Lacunar amnesia
M Major depressive disorder
Major depressive episode
Male erectile disorder
Malingering
Manic episode
Mathematics disorder
Medication-related disorder
Melancholia
Mental retardation
Minor depressive disorder
Misophonia
Mixed episode
Mood disorder
Mood episode
Morbid jealousy
Munchausen's syndrome
Munchausen's syndrome by
proxy
Multiple personality disorder
(Dissociative identity
disorder)
N Narcissistic personality
disorder
Neglect of child
Neuroleptic-related disorder
Nicotine withdrawal
Night eating syndrome
Nightmare disorder
O Obsessive-compulsive
disorder (OCD)
Obsessive-compulsive
personality disorder (OCPD)
Occupational problem
Oneirophrenia
Opioid dependence
Opioid-related disorder
Oppositional defiant disorder
(ODD)
P Pain disorder
Panic disorder
Paranoid personality disorder
Paraphilia
Parasomnia Parent-child relational problem
Parkinson's Disease
Partner relational problem
Pathological gambling
Perfectionism
Persecutory delusion
Personality change due to a general medical condition
Personality disorder
Pervasive developmental disorder (PDD)
Phase of life problem
Phencyclidine (or phencyclidine-like)-related disorder
Phobic disorder
Phonological disorder
Physical abuse
Pica
Polsubstance-related disorder
Post-traumatic embitterment disorder (PTED)
Posttraumatic stress disorder (PTSD)
Premature ejaculation
Primary hypersomnia
Primary insomnia
Psychogenic amnesia
Psychological factor affecting medical condition
Psychotic disorder
Pyromania

R

Reactive attachment disorder of infancy or early childhood
Reading disorder
Recurrent brief depression
Relational disorder
Residual schizophrenia
Retrograde amnesia
Rett's disorder
Rumination syndrome

S

Sadomasochism
Schizoaffective disorder
Schizoid personality disorder
Schizophrenia
Schizophreniform disorder
Schizotypal personality disorder
Seasonal affective disorder
Sedative-, hypnotic-, or anxiolytic-related disorder
Selective mutism
Separation anxiety disorder
Severe mental retardation
Shared psychotic disorder
Sleep disorder
Sleep terror disorder
Sleepwalking disorder
Social anxiety disorder
Social phobia
Somatization disorder
Somatoform disorder
Specific phobia
Stendhal syndrome
Stereotypic movement disorder
Stuttering
Substance-related disorder

T

Tardive dyskinesia
Transient global amnesia
Trichotillomania

Examples of Applicable Treatments

This invention may be used in conjunction with a variety of treatments, including but not limited to:

Drugs used to treat pain (for example NSAIDs, narcotics, opiates, others)
Somatotherapy (type of pharmacotherapy; biology-based treatments)
Psychiatric medications (psychoactive drugs used in psychiatry)
Antianxiety drugs (anxiolytics)
Antidepressant drugs
Antipsychotic drugs
Mood stabilizers
Shock therapy also known as convulsive therapies
Insulin shock therapy (no longer practiced)
Electroconvulsive therapy
Psychosurgery
Leukotomy (prefrontal lobotomy; no longer practiced)
Bilateral cingulotomy
Deep brain stimulation
Psychotherapy (psychology-based treatment)
Cognitive Behavior Therapy
Psychoanalysis
Gestalt Therapy
Interpersonal psychotherapy
EMDR
Behavior Therapy Exemplary Implementations Exemplary implementations are described herein, in conjunction with the attached figures. FIG. 1 illustrates an example environment 100 wherein various concepts for quantitatively assessing an individual's mental characteristics, as described throughout this disclosure, may be implemented. An evaluating entity 102 for selecting one or more stimuli for delivery to assessed individual 104 may, in some embodiments, select from or create stimuli (or combinations thereof) via a selection entity or mechanism 106 for delivery to the assessed individual via delivery device 108. Such stimuli may be represented in (e.g., stored upon) data store 110. In some embodiments, the selection entity, the delivery device, the data store, or any combination thereof, may be embodied in the same physical or virtual entity. In some embodiments, the evaluating entity may be a human evaluator. In some embodiments, the evaluating entity may be integrated into the delivery device and/or the selection entity (e.g., where the facilities thereof are integrated into a computing device). In some embodiments, the data store and/or the delivery device may not be interconnected, thereby requiring manual action from evaluating entity 102 (e.g., where the evaluating entity interfaces with the data store via the selection entity, such as a computer, to determine or receive instructions for stimuli to administer to the assessed individual, then manually uses a physical delivery device to deliver the stimuli to the assessed individual in accordance with the determined or received instructions).

Figure 2:
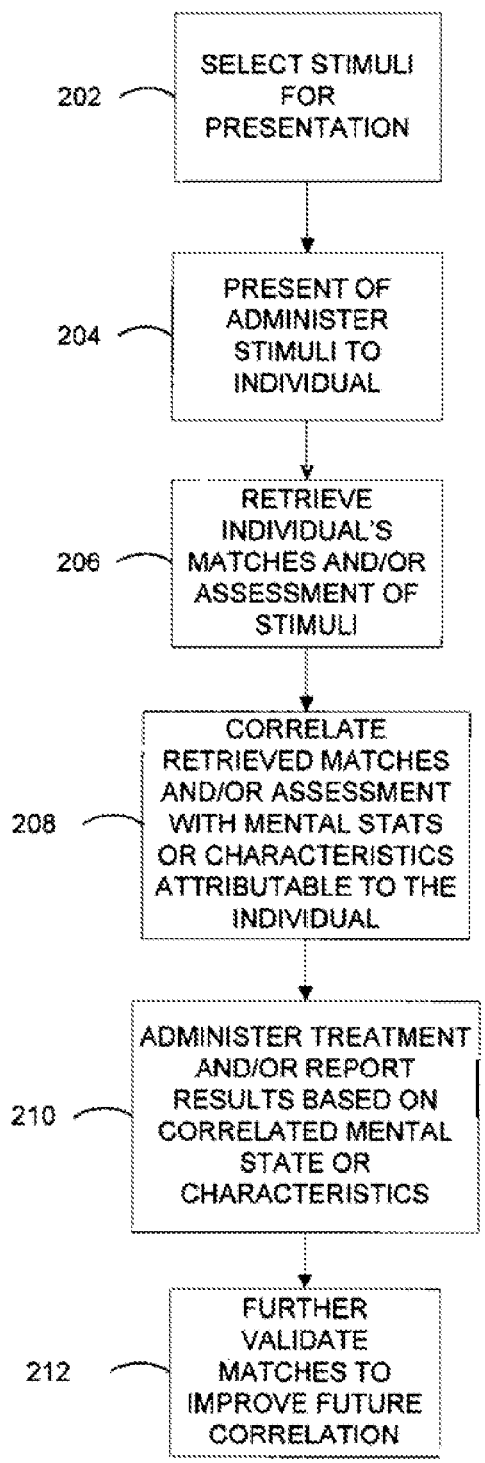
FIG. 2 shows an illustrative example of a process for quantifying an individual's mental states and/or related characteristics, in accordance with at least one embodiment.

FIG. 2. illustratively provides an example process 200 for quantitatively assessing an individual's mental state or characteristics. Stimuli are first selected 202 for presentation, e.g., to an assessed individual, by an evaluating entity. As previously described, such stimuli may be stored or represented in a data store (e.g., a database) and selected based on an initial analysis of the assessed individual's mental characteristics or states (e.g., a preliminary diagnosis). The stimuli are presented or administered 204 to the assessed individual, using one or more delivery mechanisms previously described in detail. At a time after presentation, the assessed individual's choices, matches or assessment of the presented stimuli are received 206. In some embodiments, such choices, matches or assessment may be received directly from the assessed individual. In some embodiments, they are received through an intermediary, such as a computerized user interface or human representative of the assessed individual. The received choices, matches or assessment is correlated 208 with mental states or characteristics known to be associated with the received choices, matches or assessment, and which are attributable to the assessed individual. As previously described, the correlation may in some embodiments be based on previously developed knowledge that is iteratively built, and which may in some cases be represented as data that are stored on a data store, such as a database, for retrieval. In some embodiments, the correlation is performed by a computer or computer-associated device. The correlated results (e.g., the matched mental states or characteristics), may then be reported 210, and optionally, a treatment to address the matched mental states or characteristics may be selected based on the correlated results (e.g., as appropriate for the severity or character of the underlying condition, which may be inferred or directly derived from the correlated results). Optionally, the correlated results may be further validated 212 so as to improve future correlation, e.g., via crowdsourcing techniques, iterative refinement and the like, and may also be stored upon, e.g., the data store in association with the stimuli represented as data thereon.

Figure 3A:
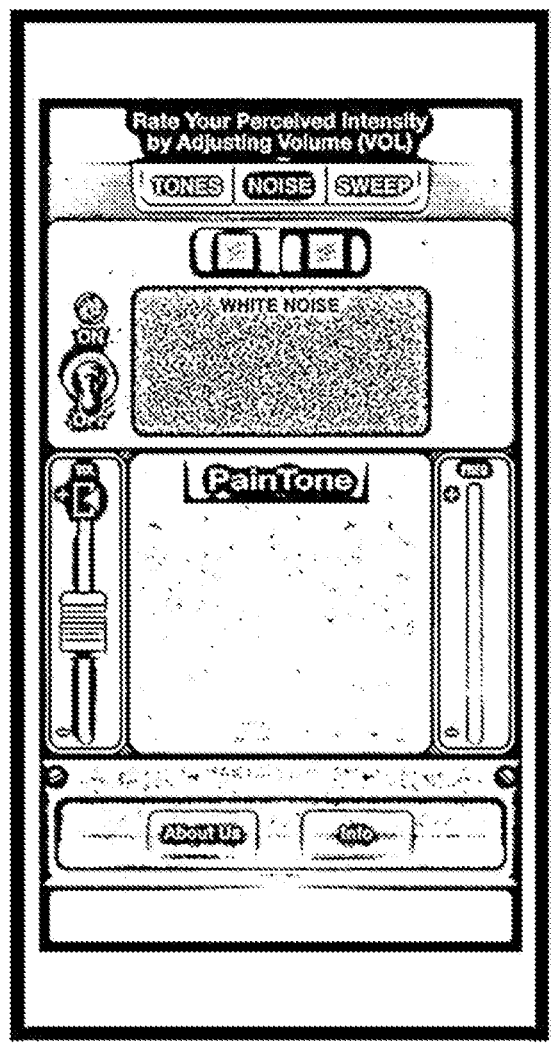
FIGS. 3A-3C show an illustrative example of a user interface (UI) in which processes and systems for quantifying mental characteristics may be implemented.
Figure 3B:
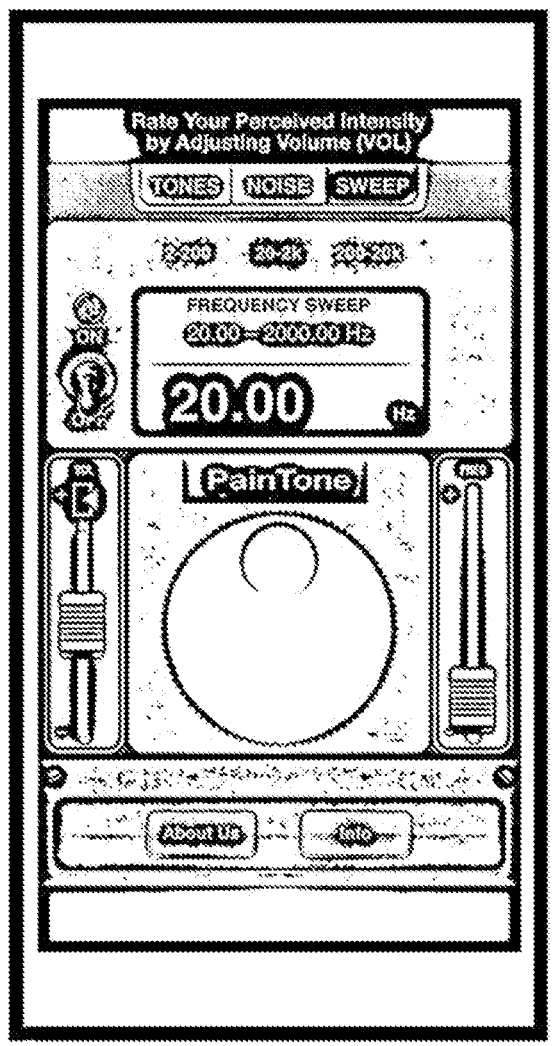
Figure 3C:
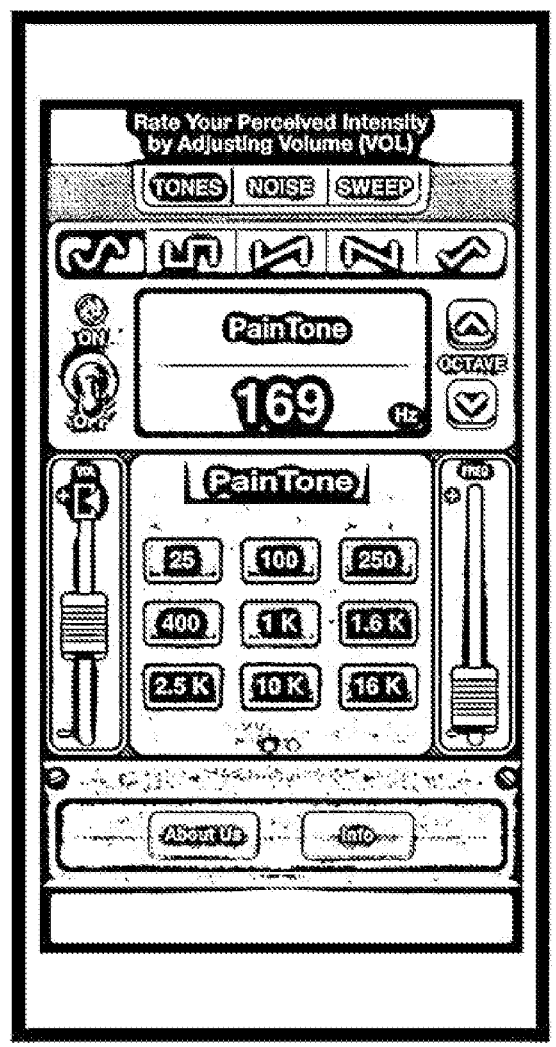
Figure 4A:
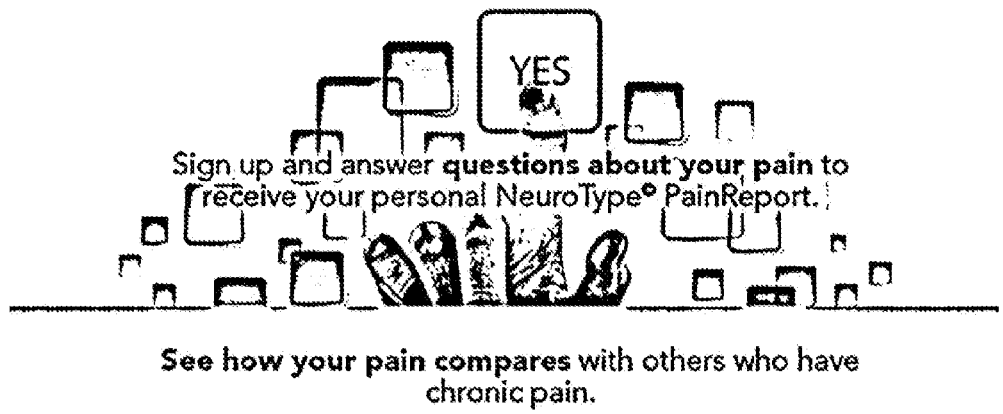
Figure 4A:
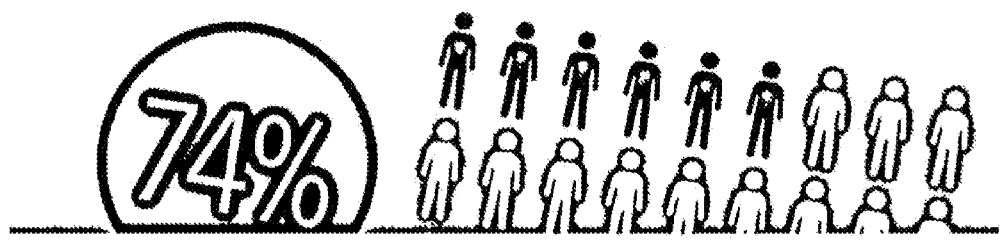
Figure 4A:
Figure 4A:
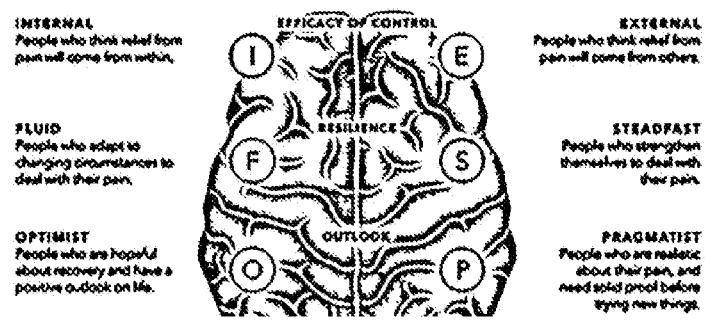
Figure 4B:
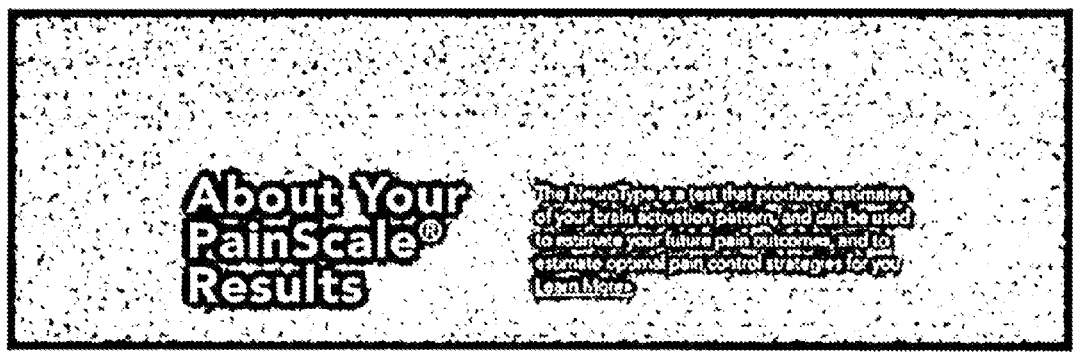
Figure 4B:
Figure 4B:
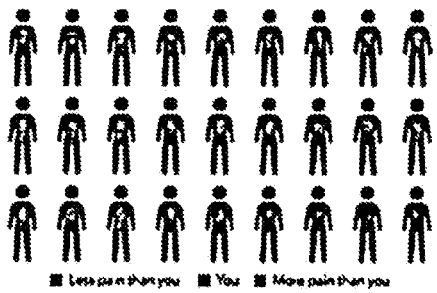
Figure 4C:
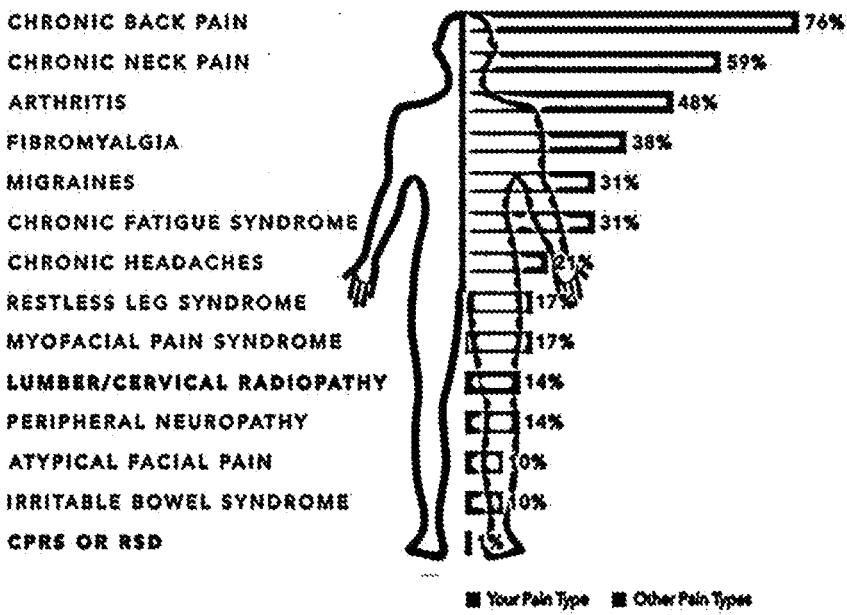
Figure 4C:
Figure 4E:
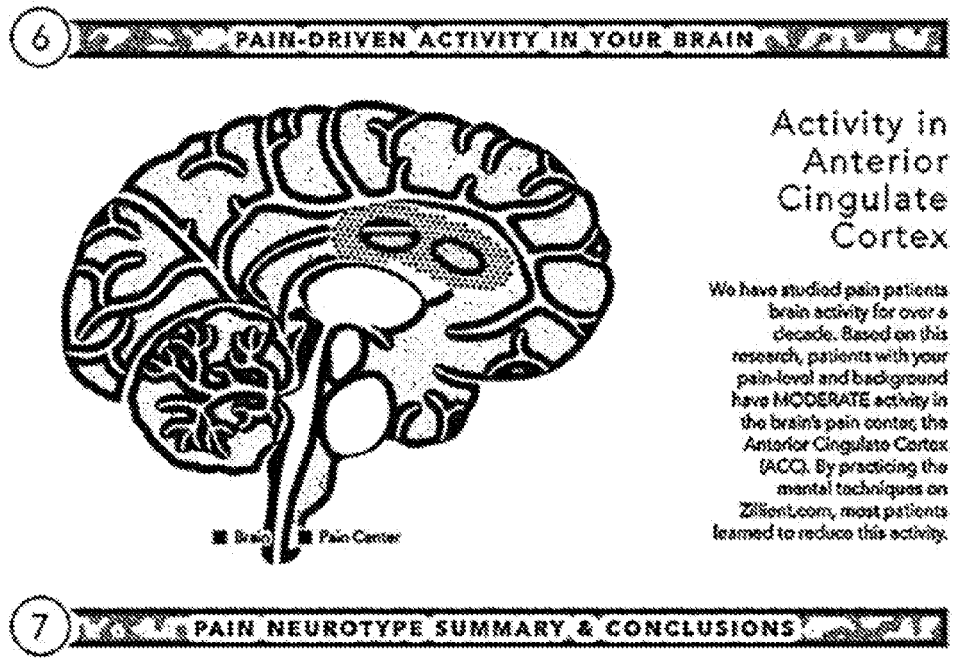
Figure 4E:
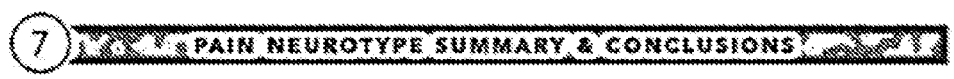
Figure 4E:
Figure 4E:
Figure 4E:
Figure 4E:

FIGS. 3A-3C illustrate an example user interface (UI) in which many concepts disclosed herein may be implemented. For example, the UI of FIGS. 3A-3C may, in some embodiments, be used for selection of stimuli, manipulation of stimuli, and administration of stimuli, as described in further detail herein. Also as described herein, such a UI may be displayed or utilized via a smartphone, computer, Web browser, tablet computer, standalone software application, and the like.

FIGS. 4A-4E illustrate an example format for communicating results of various techniques described in further detail herein. The illustrated format may be displayed as a report via, e.g., a smartphone, computer, Web browser, tablet computer, standalone software application, and the like. The illustrated format may also be printed and physically distributed. Also as described herein, the illustrated format may be disseminated to any appropriate party, including but not limited to the individual being assessed, an evaluator such as medical personal, an insurance carrier or representative thereof, to law enforcement, and the like.

General Considerations

The various techniques described herein may be partially or fully implemented using code that is storable upon storage media and computer readable media, and executable by one or more processors of a computer system. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

The specification and drawings arc, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

The brain activity of a group of people were recorded using a brain scanner while the patients practiced mental strategies.

The same group of people also filled out multiple questionnaires consisting of many questions that assessed their personality, psychology, symptoms, disease states, treatments, and pain experience. Patients filled out these questionnaires at multiple times throughout the treatment program, including prior to treatment and after treatment. This allowed measures of each persons improvement or worsening of symptoms.

Upon completion of the treatment program, patterns of brain activity were correlated across patients with patient's answers to the different questionnaire questions. That is, for each questionnaire question, a characteristic pattern of brain activity was computed for each possible answer to the question.

The characteristic patterns of brain activity (and the questionnaire answers associated with them) were correlated across patients with the effectiveness of specific treatment programs and parameters. That is, a determination was made of which patterns of brain activity (and patterns of answers to questionnaire questions) were associated with which successful or unsuccessful treatments.

The questions that best predicted the effectiveness of treatment were selected from the questionnaires. Questions that best predicted patients outcomes in terms of their changes in symptoms with treatment or without treatment were also selected from the questionnaires. The questions were categorized into separate broad dimensions of the person's pain experience, some of the dimensions including a) pain or symptom intensity, b) perception of the efficacy of his/her control over pain or symptoms, c) resilience in adapting to pain or symptoms, d) outlook on chances for relief from pain or symptoms, and e) degree of acceptance of pain or symptoms as an aspect of daily life.

Example 2

Based, for example, on the questions, answers, patterns and correlations previously discussed in connection with Example 1, a report such as a neurotype report may be generated based on a person's answers to these questions. Once the person submits his/her answers to the questions, for example on a website, an algorithm analyzes the person's data and immediately generates a customized report based on the visitor's answers. This report compares the person's answers to a database of prior people's answers. The algorithm can determine the percentile of the person's responses for each question or combination of questions with prior subjects. The algorithm can determine the category of the person's responses for each question or combination of questions with prior subjects.

The report and algorithm described in this Example 2 may, for example, be used in conjunction with any of the aspects of this invention described herein. For example, if a subject answers questions, this may be used to determine their relative pain intensity compared to that of other subjects, their personality type relative to that of other subjects, or their predicted change in symptoms at any future time point based on changes measured in similar subjects. The data from a person's pain ratings using the current invention, for example based upon forming a correlation between their pain or symptoms with sounds or other stimuli, may be used as input to this algorithm. In addition, the results of this algorithm may be used to refine the person's pain rating based upon their correlation between their pain or symptoms with sounds or other stimuli.

What is claimed is:

1. A computer-implemented method of assessing pain experienced by users, the method comprising:

determining, by a computing device, a sound threshold level for a user, wherein the determined sound threshold level for the user represents a minimum auditory characteristic that the user is able to hear;

receiving, at the computing device, input from the user that identifies one or more sound characteristics that match one or more aspects of a pain experienced by the user, wherein receiving the input comprises:

outputting an audible sound to the user, and receiving, through a user interface, user input that indicates a response regarding at least one characteristic of the audible sound; and determining, by the computing device, a measurement of the pain experienced by the user based, at least in part, on the audible sound output to the user, the determined sound threshold level for the user, and the response from the user as matching the one or more aspects of the pain.

2. The computer-implemented method of claim 1, wherein the one or more sound characteristics include amplitude.

3. The computer-implemented method of claim 1, wherein the one or more sound characteristics include frequency.

4. The computer-implemented method of claim 1, wherein the one or more aspects of the pain include an intensity of the pain.

5. The computer-implemented method of claim 1, wherein the one or more aspects of the pain include a quality of the pain.

6. The computer-implemented method of claim 1, further comprising:

receiving information that identifies a particular type of the pain experienced by the user.

7. The computer-implemented method of claim 1, further comprising:

comparing the measurement to results from sound-based pain assessments from others users.

8. The computer-implemented method of claim 7, further comprising:

receiving information that identifies a particular type of the pain experienced by the user, and wherein the results comprise a distribution of measurements for pain experienced by the other users of the particular type.

9. The computer-implemented method of claim 1, further comprising:

determining, by the computing device, a treatment for the pain experienced by the user based, at least in part, on the measurement;

outputting, by the computing device, information describing the treatment.

10. The computer-implemented method of claim 1, further comprising:

outputting, by the computing device, information that describes the measurement of the pain.

11. The computer-implemented method of claim 1, wherein the information is determined and output in response to and within a threshold amount of time of the input from the user being received and the measurement being determined.

12. The computer-implemented method of claim 1, further comprising:

determining the information based on a comparison of the measurement with other measurements.

13. The computer-implemented method of claim 1, further comprising:

determining a change in the user's pain over a period of time based on a comparison of two or more measurements for the user.

14. The computer-implemented method of claim 13, further comprising:
determining an effectiveness of a treatment for the user based, at least in part, on the change in the user's pain over the period of time.

15. The computer-implemented method of claim 14, wherein the effectiveness of the treatment is additionally determined based on a comparison of the change over the period of time with a level of change experienced by a different group of individuals receiving a different treatment.

16. The computer-implemented method of claim 1, wherein the response comprises selection of a value of the at least one characteristic of the audible sound from among a plurality of values.

17. The computer-implemented method of claim 1, wherein:
the audible sound is output with a starting value for the at least one characteristic of the audible sound, and
the response comprises selection of either a first user interface feature to increase the starting value or a second user interface feature to decrease the starting.

18. The computer-implemented method of claim 1, wherein the computing device is calibrated to output the audible sound at one or more calibrated levels.

19. The computer-implemented method of claim 1, further comprising:
receiving user selection of one or more of: stimuli and parameters of the stimuli;
outputting user interface features for adjusting values corresponding to the selected one or more of: the stimuli and parameters of the stimuli; and
adjusting the audible sound based on input that is received through the user interface features.

20. The computer-implemented method of claim 1, further comprising:
comparing the determined measurement with other information provided by or observed about the user that indicates one or more aspects of the pain experienced by the user.

21. The computer-implemented method of claim 1, wherein the determining the sound threshold level for the user includes determining more than one sound threshold level for the user, where each of the more than one sound threshold levels represents a minimum auditory characteristic that the user is able to hear.

22. A computer-implemented method of assessing pain experienced by users, the method comprising: determining, by a computing device, a minimum auditory threshold for a user; receiving, at the computing device, input from the user that identifies one or more sound characteristics that match one or more aspects of a pain experienced by the user, wherein receiving the input comprises: outputting an audible sound to the user, and receiving, through a user interface, user input that indicates a response regarding at least one characteristic of the audible sound; and determining, by the computing device, a measurement of the pain experienced by the user based, at least in part, on the minimum auditory threshold of the user, the audible sound output to the user and the response from the user as matching the one or more aspects of the pain.

* * * * *